United States Patent [19]

Liang

[11] Patent Number: 5,578,004
[45] Date of Patent: Nov. 26, 1996

[54] FEED DRUG INJECTOR

[76] Inventor: Kun-Shan Liang, No. 135, Lane 530, Sec. 1, Chung Shan Road, Chang Hua City, Taiwan

[21] Appl. No.: 603,347

[22] Filed: Feb. 20, 1996

[51] Int. Cl.⁶ ................................................. A61M 31/00
[52] U.S. Cl. ................................................. 604/77; 606/236
[58] Field of Search ............................... 604/77, 73, 212; 606/234, 235, 236

[56] References Cited

U.S. PATENT DOCUMENTS

| | | | |
|---|---|---|---|
| 3,022,915 | 2/1962 | Mullin | 606/234 |
| 4,078,566 | 3/1978 | Urban, Jr. | 604/77 |
| 5,197,974 | 3/1993 | Scarpelli et al. | 606/236 X |
| 5,478,325 | 12/1995 | Fu-Hsiang | 604/77 X |

Primary Examiner—John D. Yasko
Attorney, Agent, or Firm—Beveridge, DeGrandi, Weilacher & Young, L.L.P.

[57] ABSTRACT

A feed drug injector comprises a nipple device, a nipple plug inserted in the nipple device, a front end of a cylinder inserted in the nipple plug, and a push rod inserted in the cylinder. The nipple device has a base and a nipple head. Two inner recesses are formed on the inner periphery of the base. A passage is formed in the nipple head. A Y-shaped hole is formed in the front of the passage. A bevel is formed on the front surface of the nipple head. Three apertures which are formed on the bevel and two front sides of the nipple head communicate with the Y-shaped hole. The nipple plug has a disk with an inner thread, a Y-shaped bar, and three circular holes formed on the disk. Two protrusions are disposed on the outer periphery of the disk. The protrusion engages with the inner recess. The cylinder the disk.

1 Claim, 3 Drawing Sheets

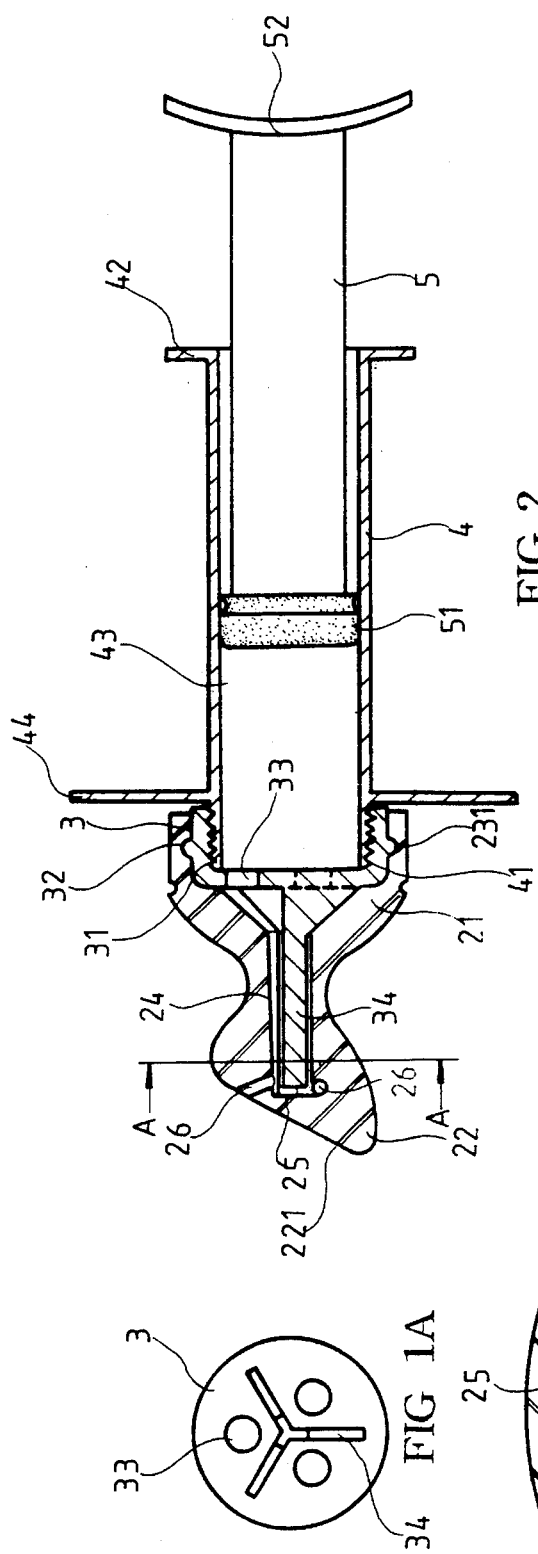
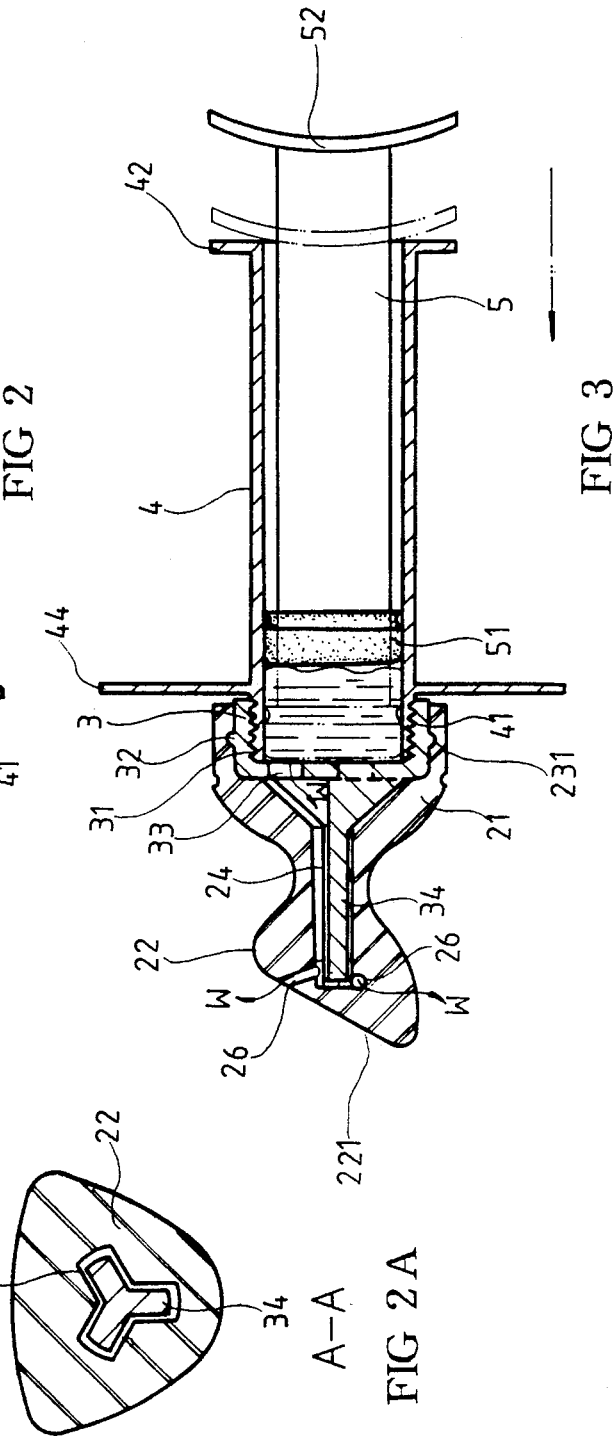

FEED DRUG INJECTOR

BACKGROUND OF THE INVENTION

The invention relates to a feed drug injector. More particularly, the invention relates to a feed drug injector which can feed medicinal liquid into fauces directly.

The children may vomit medicinal liquid because of the bitter taste of the medicinal liquid. Some feeding injectors have very narrow inner passages so that the medicinal liquid can only pass through the inner passage under pressure. Most feeding injectors have shapes similar to the shape of a syringe. The needle of the syringe is replaced by a tube with a very narrow inner passage. Since the inner passage is too straitened, the residual of the medicinal liquid will remain in the inner passage. It is very difficult to remove the residual of the medicinal liquid by washing the inner passage. The residual of the medicinal liquid will be deteriorated for a long period of time. The deteriorated medicinal residual will become very toxic, mildewed, or stinking. Therefore, the deteriorated medicinal residual will contaminate the fresh medicinal liquid after they are mixed in the inner passage. Further, the inner passage is very short so that the medicinal liquid cannot be directed to the predetermined direction precisely. If the inner passage is elongated, it will hurt the throat and the oral cavity of the user.

SUMMARY OF THE INVENTION

An object of the invention is to provide a feed drug injector which can feed medicinal liquid into fauces directly or through the tongue quickly before the user tasting the bitter taste of the medicinal liquid.

Another object of the invention is to provide a feed drug injector which can direct the medicinal liquid into the predetermined direction precisely.

Another object of the invention is to provide a feed drug injector which can be assembled or detached easily.

Another object of the invention is to provide a feed drug injector which can be cleaned thoroughly so that the residual of the medicinal liquid will not remain therein.

However, the structure of the present invention is not a simple combination of a syringe and a nipple. The structure and function of the nipple device of the present invention is significantly different from those of the conventional nipple. The nipple device is not for sucking but for directing and delivering medicinal liquid into fauces directly or through the tongue quickly. The combination of the nipple plug and the nipple device can accelerate the flow of the medicinal liquid into the predetermined direction and position precisely. Each portion of the present invention can be cleaned thoroughly so that the residual of the medicinal liquid will not remain.

Accordingly, a feed drug injector comprises a nipple device, a nipple plug inserted in the nipple device, a front end of a cylinder connecting the nipple plug, and a push rod inserted in the cylinder. The nipple device has a hollow circular base and a generally duckbilled nipple head extending forward from the base. At least two inner recesses are formed on the inner periphery of the base. A truncated-cone shaped passage is formed in the nipple head. A Y-shaped hole is formed in the front of the truncated-cone shaped passage. A bevel is formed on the front surface of the nipple head. Three apertures which are formed on the bevel and two front sides of the nipple head respectively communicate with the Y-shaped hole. The nipple plug has a hollow disk with an inner thread, a Y-shaped bar extending forward from the disk, and three circular holes formed on the top surface of the disk spacedly and separated by the Y-shaped bar. Two protrusions are disposed on the outer periphery of the disk. The protrusion engages with the corresponding inner recess. The Y-shaped bar is inserted in the nipple head. The disk is inserted in the base. The cylinder has a round plate on the front portion, an outer thread and an orifice at the front end, and a round flange at the rear end. The outer thread of the cylinder engages with the inner thread of the disk. The push rod has a pad plunger at the front end and a handle bar at the rear end.

BRIEF DESCRIPTION OF THE DRAWINGS

FIG. 1A is a top plan view of a nipple plug of the invention;

FIG. 2 is a cross-sectional assembly view of an empty feed drug injector;

FIG. 2A is an enlarged top plan view of a Y-shaped bar in a Y-shaped recess;

FIG. 3A is a side elevational view of a portion of a feed drug injector in the oral cavity; and FIG. 3B is a top plan view of a feed drug injector in the oral cavity.

DETAILED DESCRIPTION OF THE INVENTION

Figure 1:
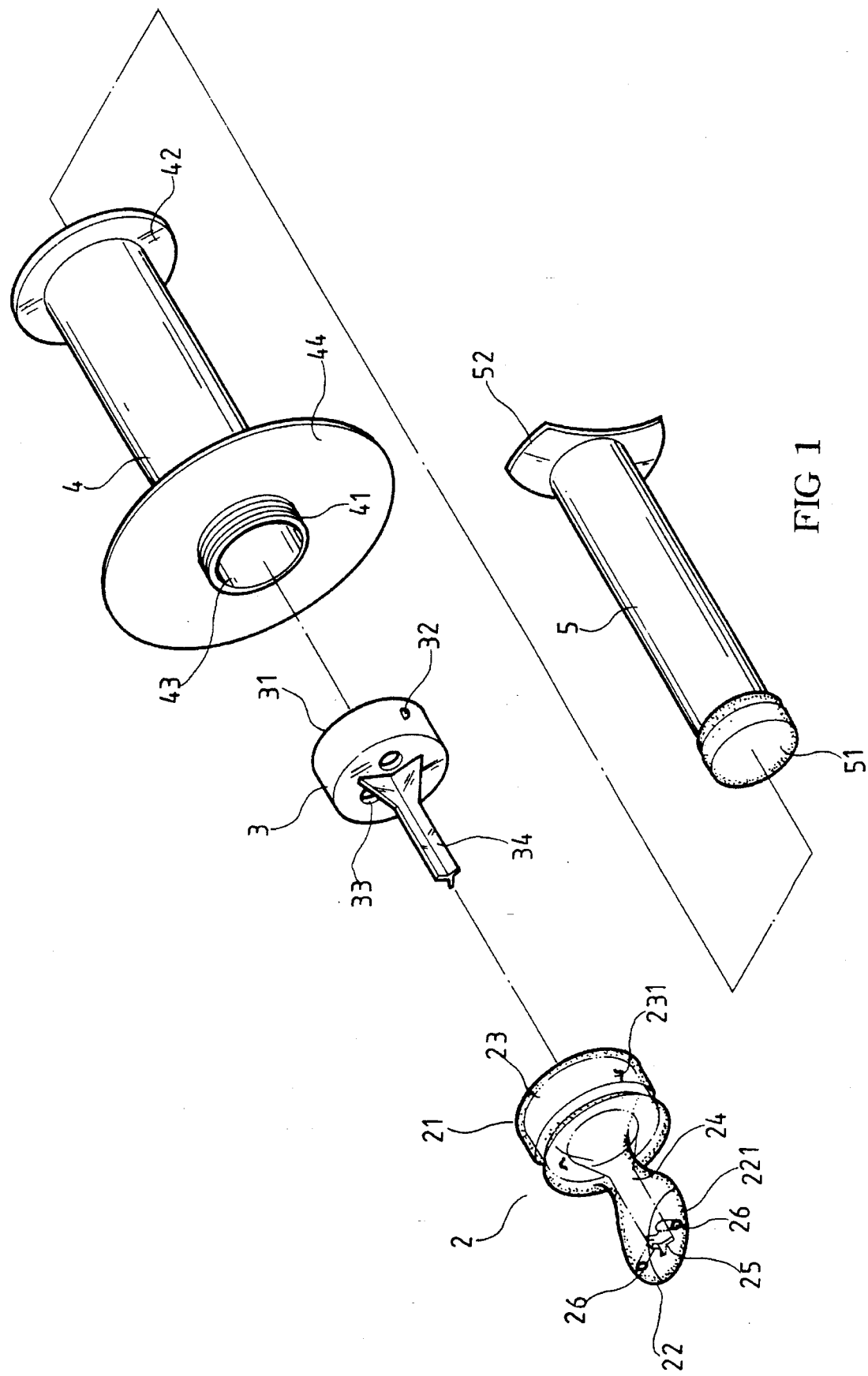
FIG. 1 is a perspective exploded view of a feed drug injector of a preferred embodiment in accordance with the invention.
Figure 3:
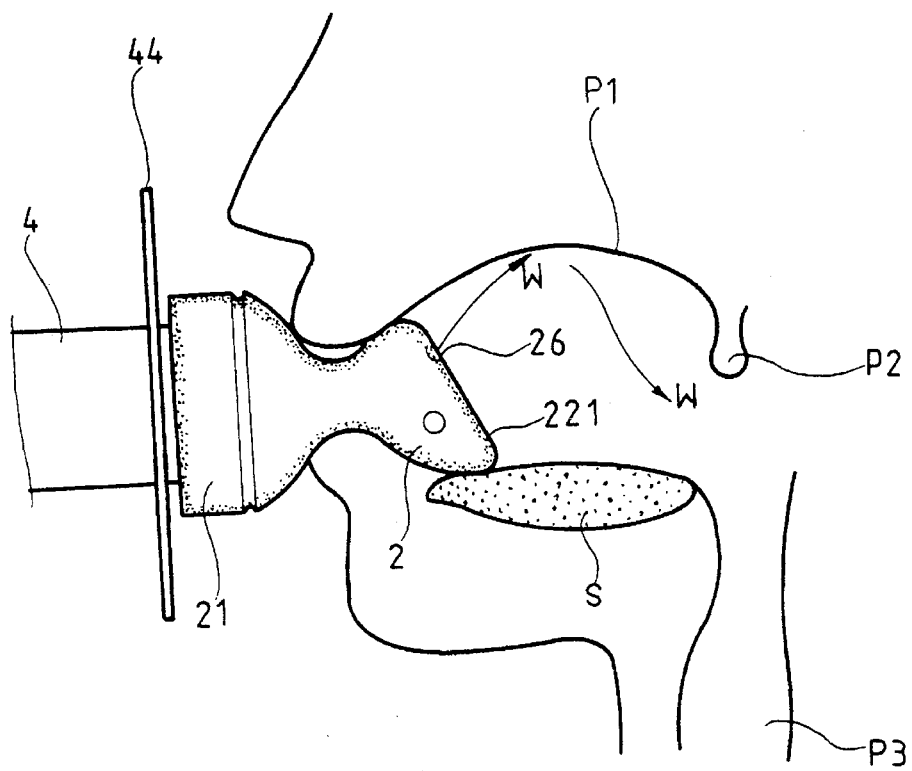
FIG. 3 is a cross-sectional assembly view of a feed drug injector with a medicinal liquid.
Figure 3:
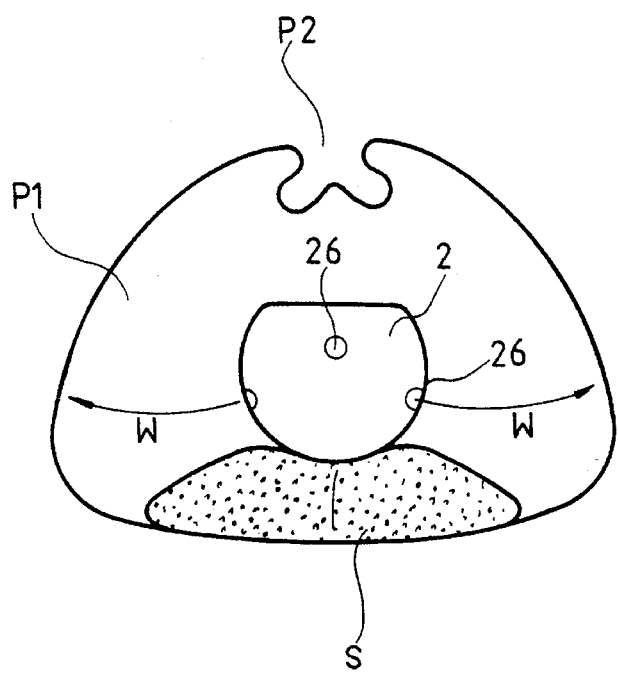

Referring to FIGS. 1 to 3, a feed drug injector comprises a nipple device 2, a nipple plug 3 inserted in the nipple device 2, a front end of a cylinder 4 connecting the nipple plug 3, and a push rod 5 inserted in the cylinder 4. The nipple device 2 has a hollow circular base 21 and a generally duckbilled nipple head 22 extending forward from the base 21. At least two inner recesses 231 are formed on the inner periphery of the base 21. A truncated-cone shaped passage 24 is formed in the nipple head 22. A Y-shaped hole 25 is formed in the front of the truncated-cone shaped passage 24. A bevel 221 is formed on the front surface of the nipple head 22. Three apertures 26 which are formed on the bevel 221 and two front sides of the nipple head 22 respectively communicate with the Y-shaped hole 25. The nipple plug 3 has a hollow disk 31 with an inner thread, a Y-shaped bar 34 extending forward from the disk 31, and three circular holes 33 formed on the top surface of the disk 31 spacedly and separated by the Y-shaped bar 34. Two protrusions 32 are disposed on the outer periphery of the disk 31. The protrusion 32 engages with the corresponding inner recess 231. The Y-shaped bar 34 is inserted in the nipple head 22. The disk 31 is inserted in the base 21. The cylinder 4 has a round plate 44 on the front portion, an outer thread 41 and an orifice 43 at the front end, and a round flange 42 at the rear end. The outer thread 41 of the cylinder 4 engages with the inner thread of the disk 31. The push rod 5 has a pad plunger 51 at the front end and a handle bar 52 at the rear end.

Referring to FIGS. 3, 3A and 3B, the cylinder 4 contains medicinal liquid W therein. The nipple head 22 is placed on the tongue S of the oral cavity P1 so that medicinal liquid W flows out via the larynx P2 to reach the throat P3. The mouth is blocked by the round plate 44. Since the medicinal liquid W does not touch the tongue S, the tongue S will not taste the medicinal liquid W. When the push rod 5 pushes the medicinal liquid W into the nipple plug 3, the medicinal liquid W flows from the circular holes 33 to the passage 24, and to the apertures 26. Thus the medicinal liquid W can bypass the tongue S and enters the throat P3 directly.

The invention is not limited to the above embodiment but various modification thereof may be made. Further, various changes in form and detail may be made without departing from the scope of the invention.

I claim:

1. A feed drug injector comprising:

a nipple device having a hollow circular base and a generally duckbilled nipple head extending forward from said base;

at least two inner recesses formed on an inner periphery of said base;

a truncated-cone shaped passage formed in said nipple head;

a Y-shaped hole formed in a front of said truncated-cone shaped passage;

a bevel formed on a front surface of said nipple head;

three apertures which are formed on said bevel and two front sides of said nipple head, respectively, communicating with said Y-shaped hole;

a nipple plug having a hollow disk with an inner thread, a Y-shaped bar extending forward from said disk, and three circular holes formed on a top surface of said disk spacedly and separated by said Y-shaped bar;

at least two protrusions disposed on an outer periphery of said disk;

each of said protrusions engaging with each of said corresponding inner recesses;

said Y-shaped bar inserted in said nipple head;

said disk inserted in said base;

a cylinder having a round plate on a front portion, an outer thread and an orifice at a front end, and a round flange at a rear end of said cylinder;

said outer thread of said cylinder engaging with said inner thread of said disk;

a push rod having a pad plunger at a front end and a handle bar at a rear end of said push rod; and said push rod inserted in said cylinder.

* * * * *